United States Patent [19]
Banerian

[11] Patent Number: 5,611,428
[45] Date of Patent: Mar. 18, 1997

[54] ANGIOGRAPHY GUIDE WIRE CONTAINER

[76] Inventor: Kirk Banerian, 7105 Glenburnie, Clarkston, Mich. 48346

[21] Appl. No.: 470,937

[22] Filed: Jun. 6, 1995

[51] Int. Cl.$^6$ .............................. B65D 83/10; A61B 5/00
[52] U.S. Cl. ....................... 206/364; 128/772; 206/210; 206/438; 604/171
[58] Field of Search ........................... 604/171; 206/364, 206/363, 409, 438, 210; 422/20, 28; 128/772

[56] References Cited

U.S. PATENT DOCUMENTS

| | | | |
|---|---|---|---|
| 3,100,487 | 8/1963 | Bathish | 206/364 X |
| 3,683,928 | 8/1972 | Kuntz | 206/364 X |
| 3,854,479 | 12/1974 | Duke | 206/364 X |
| 4,607,746 | 8/1986 | Stinnette . | |
| 4,721,123 | 1/1988 | Cosentino et al. | 604/171 X |
| 4,754,877 | 7/1988 | Johansson et al. | 206/364 |
| 4,886,500 | 12/1989 | Lazarus . | |
| 4,936,448 | 6/1990 | Hollaway | 206/364 |
| 5,125,416 | 6/1992 | Phillips | 206/409 X |
| 5,135,516 | 8/1992 | Sahatjian et al. . | |
| 5,242,428 | 9/1993 | Palestrant . | |
| 5,290,242 | 3/1994 | Vaillancourt . | |
| 5,310,524 | 5/1994 | Campbell et al. . | |

*Primary Examiner*—Bryon P. Gehman
*Attorney, Agent, or Firm*—Gifford, Krass, Groh, Sprinkle, Patmore, Anderson & Citkowski, P.C.

[57] ABSTRACT

There is disclosed herein a container for use in storing, cleansing, and moistening guide wires between uses during angiographic procedures. The container has a base and at least one upwardly and inwardly extending side wall. The container may also have a plurality of standoff members to keep the coiled guide wire from touching the base and side walls of the container. A bathing solution may also be disposed within the container to moisten and cleanse the coiled guide wire.

31 Claims, 3 Drawing Sheets

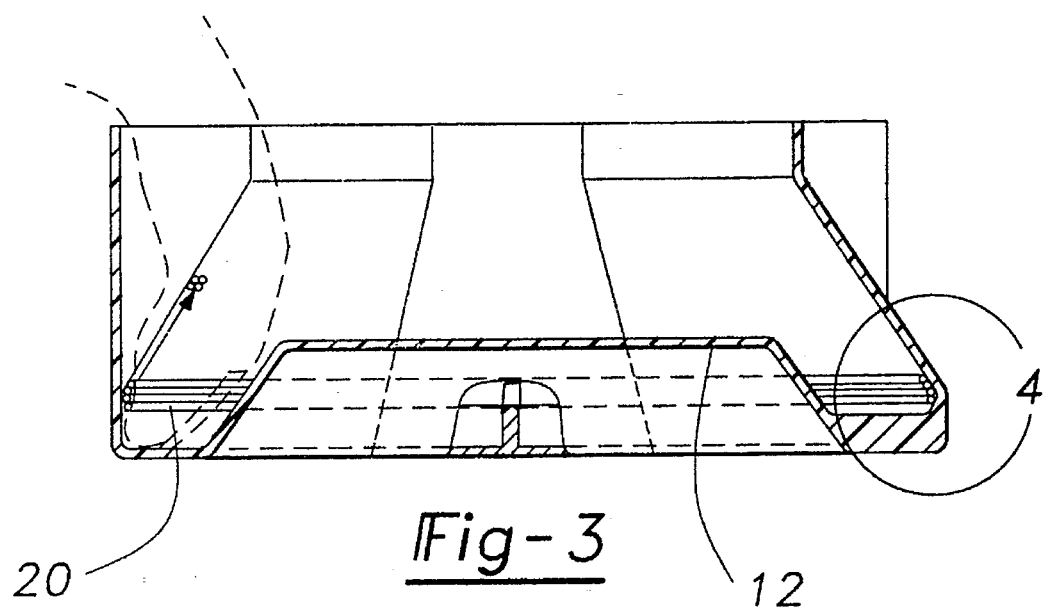
Fig-3
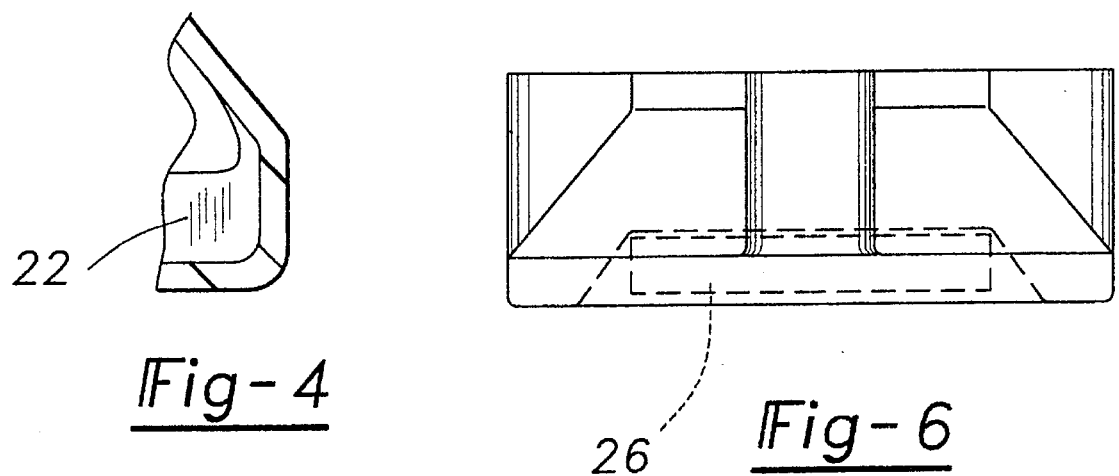
Fig-4
Fig-6
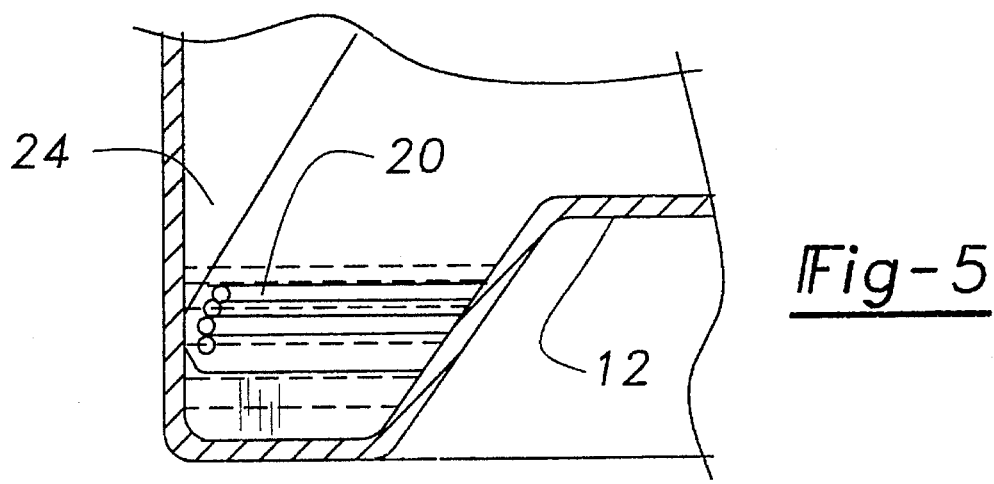
Fig-5

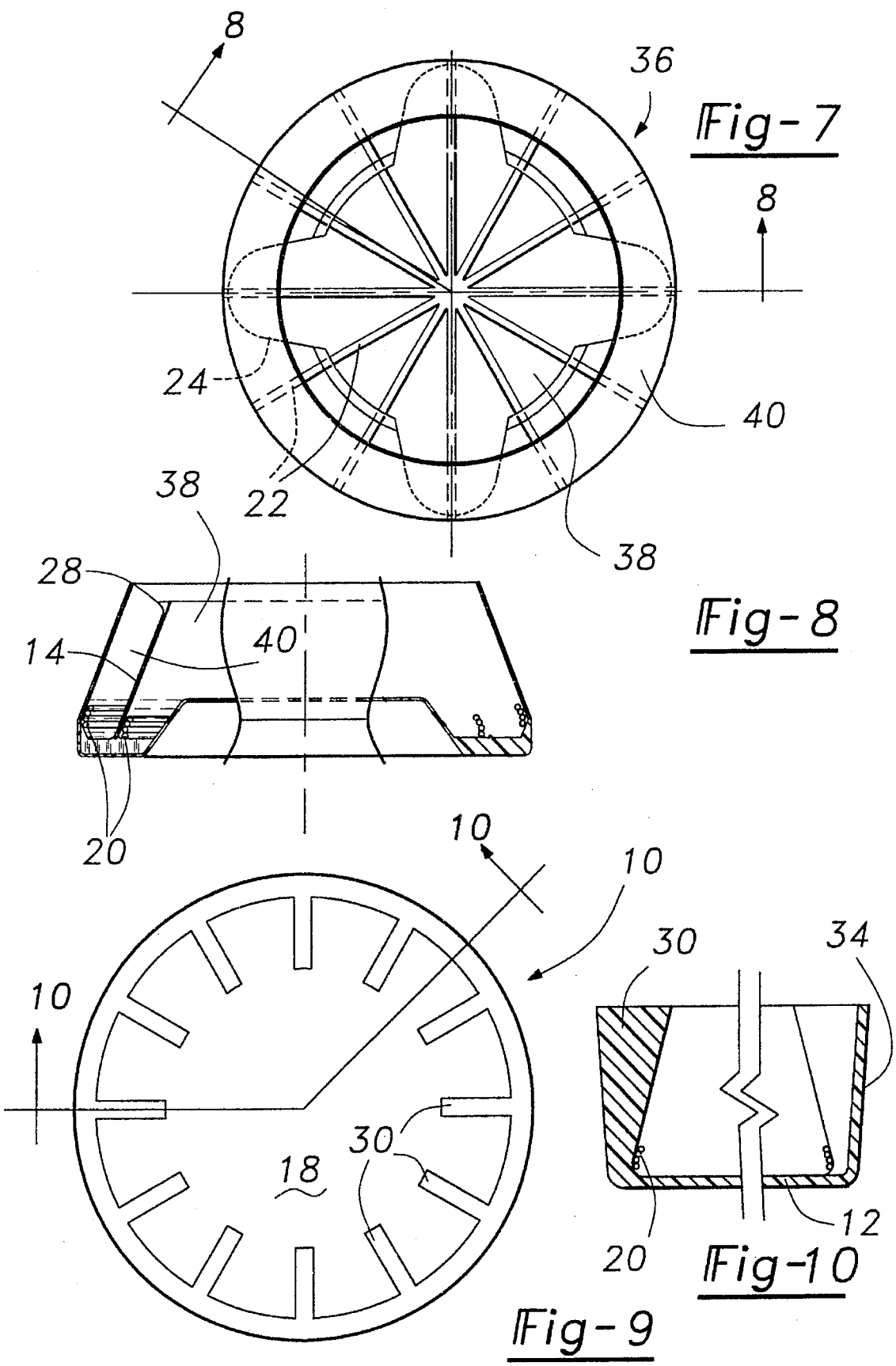

5,611,428

ANGIOGRAPHY GUIDE WIRE CONTAINER

BACKGROUND OF THE INVENTION

I. Field of the Invention:

The present invention relates generally to containers and, more particularly, to a container for holding angiography guide wires, or other elongated, flexible medical devices, in between uses during medical procedures.

II. Description of the Prior Art

Certain medical procedures involve the insertion of a catheter into the human body, injecting a contrast material through the catheter, and then obtaining images of those portions of the body. In this fashion, various abnormalities that are in the body can be detected.

In order to insert a catheter into the appropriate portions of the body, a guide wire for the catheter must first be inserted. Initially, a needle is used to enter the body. A guide wire is then inserted through the needle into the body, after which the needle is removed. A catheter is then inserted over the guide wire, the guide wire thereby "guiding" the catheter into the appropriate position. Once the catheter is in place, the guide wire is then removed so that the contrast material can be injected though the catheter. Problems arise in finding a means for containing the guide wire between uses during each procedure.

At the present time, the handling of guide wires outside of the catheter during angiography is both awkward and inefficient. During angiography, the angiographer must insert the guide wire through the needle hub to gain catheter access, as well as insert and remove the guide wire for each artery selectively catherized. Additionally, if a guide wire remains in a catheter for prolonged periods of time (i.e., in excess of two minutes) there is danger of embolic sequelae. As a result, the angiographer must remove the guide wire, flush clean the catheter, and thereafter reinsert the guide wire. This requires even additional handling of the guide wire when difficult arteries need to be accessed. A guide wire is typically inserted and removed from a patient about a half dozen times during a four vessel cerebral angiogram. For more complex cases such as spinal angiograms, a guide wire may be inserted and removed from the patient a dozen times or more.

Each time the guide wire is removed from the patient, it is wiped clean of the adherent blood, coiled to a more manageable size, and stored either by wrapping the loose end of the guide wire around the coil, or placing a weighted object on the coiled guide wire to prevent it from uncoiling or "springing open." Each time the guide wire is removed from the catheter, it comes in contact with air, allowing residual adherent blood to dry, harden, and form a potential embolic nidus. Furthermore, even though a guide wire may be carefully wiped, a certain amount of residual blood will always remain on the surface of the guide wire. An additional problem is that the unstable guide wire can become contaminated by falling onto the floor or coming into contact with an unclean surface in between uses. When this happens, the contaminated guide wire must be discarded, and replaced by a sterile guide wire.

A further problem with the present system is that after each time the guide wire is removed from the catheter, an angiographer must use both hands to close the catheter valve so as to prevent the backflow of blood from the catheter. Since both hands must be used to close the catheter valve, it is exceedingly difficult for one person to also wipe, coil, and find a suitable resting spot for the guide wire. When the guide wire is next needed, it must be carefully retrieved and unwrapped, so that it does not "spring open." When using a guide wire with a hydrophilic coating, (particularly useful for reaching difficult and tortuous arteries), there is an additional step of moistening the guide wire which must be done prior to each insertion.

SUMMARY OF THE PRESENT INVENTION

The present invention provides a device which overcomes all of the above-mentioned disadvantages of the previously-known methods of storing, cleaning, and moistening the guide wires during anglographic procedures.

In brief, the present invention comprises a container for use in angiographic procedures. The container comprises a base, and side walls which extend upwardly and inwardly from the base. The container is open at the top so that a coiled guide wire can be placed inside the container. The cross sectional area of the opening is smaller than the cross sectional area of the base, and the opening and the base may be of complementary shape.

The invention further comprises a plurality of standoff members extending from the sides and/or base of the container in order to suspend the coiled guide wire in a bathing solution that may be disposed inside the container. At least one finger slot aids in the removal of the coiled guide wire from the container during the angiographic procedure. The guide wire container can be attached to any area around a patient where it is most needed.

BRIEF DESCRIPTION OF THE DRAWINGS

A better understanding of the present invention will be had upon reference to the following detailed description, when read in conjunction with the accompanying drawings, wherein like referenced numerals refer to parts throughout the several views, and in which:

FIG. 3 is a cross-sectional view of the container of the present invention, taken along lines 3—3 of FIG. 2;

FIG. 4 is an enlarged view of circle 4, taken from FIG. 3, showing a stand-off member;

FIG. 5 is an enlarged view of a guidewire suspended in the container of the present invention;

FIG. 6 is a cross-sectional view showing the optional vibrating means;

FIG. 7 is a plan view of an alternate embodiment of the container of the present invention showing nested container chambers;

FIG. 8 is a cross-sectional view of nested containers, taken along lines 8—8 of FIG. 7;

FIG. 9 is a plan view of an alternate embodiment of the container of the present invention showing guide rails; and FIG. 10 is a cross-sectional view taken along lines 10—10 of FIG. 9.

DETAILED DESCRIPTION OF A PREFERRED EMBODIMENT OF THE PRESENT INVENTION

Figure 1:
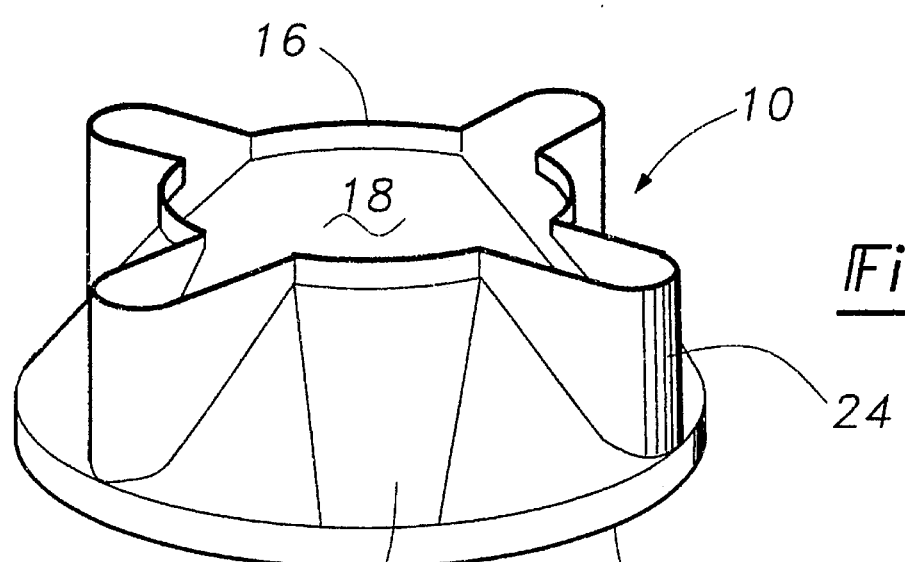
FIG. 1 is a perspective view of the container of the present invention.
Figure 2:
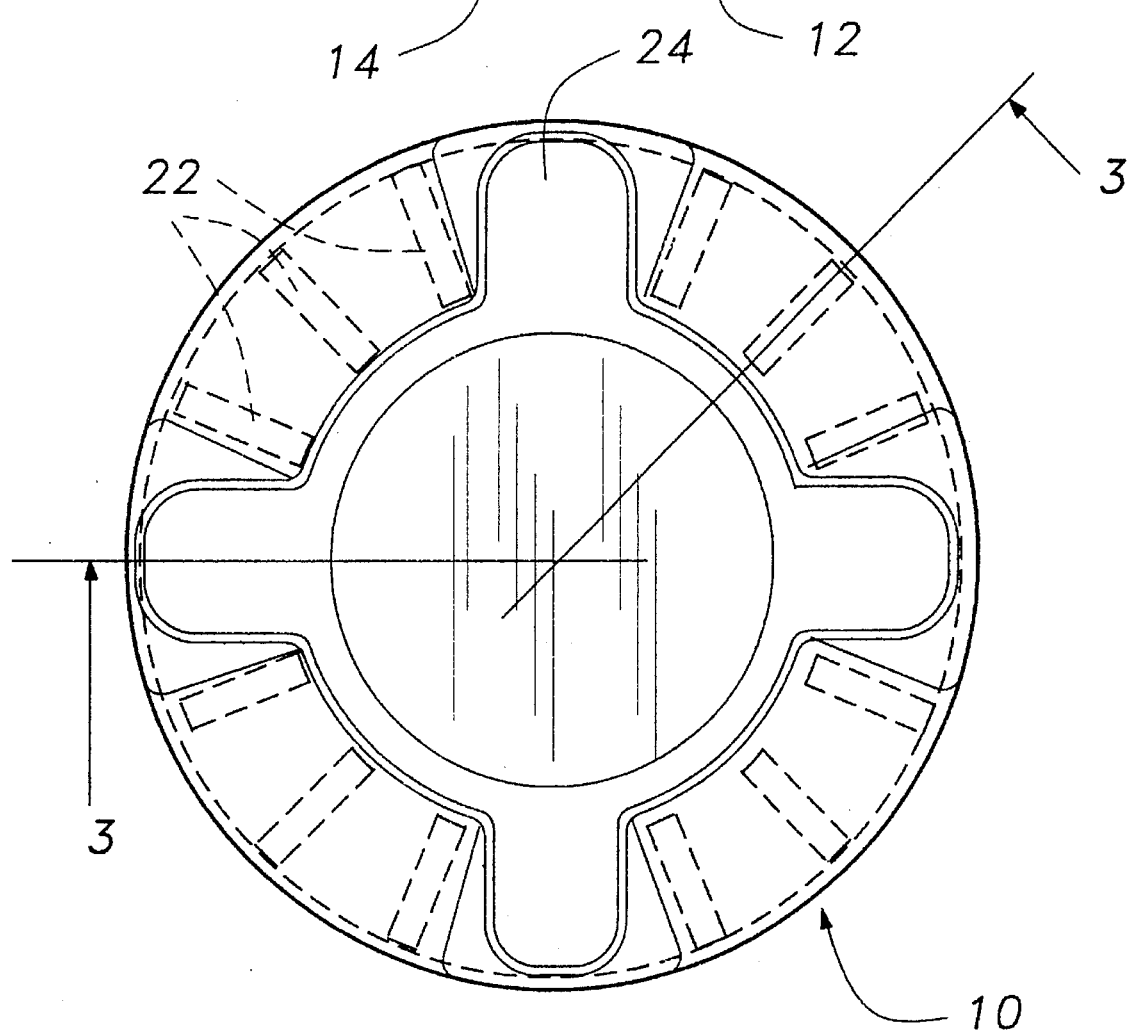
FIG. 2 is a plan view of the container of the present invention.

With reference first to FIGS. 1–5, perspective, plan and cross-sectional views of the container 10 of the present invention is thereshown. The container 10 has a base 12, and side walls 14 which extend upwardly and inwardly from the base 12. The upper edges 16 of the sidewalls 14 form an opening 18 in the container 10 through which the coiled guide wire 20 can be inserted and removed. The cross-sectional area of the opening 18 is smaller than the cross-sectional area of the base 12. Both the opening 18 and the base 12 may be of a complementary shape. Once placed through the opening 18, the potential energy in a coiled guide wire 20 will drive the guide wire 20 toward the base 12 of the container 10.

In one preferred embodiment of the invention, a plurality of standoff members 22 extend upwardly from the inner surface of the base 12. The standoff members 22 can also extend inwardly from the inner surface of the sidewalls 14. The standoff members 22 help to keep the coiled guide wire 20 suspended away from the base 12 and sides 14 of the container 10.

The container 10 of the present invention can also have one or more finger slots 24 extending outwardly from the opening 18 of the container 10 to a point at or near the base 12 of the container 10. The purpose of these finger slots 24 or protrusions is to allow easy removal of the coiled guide wire 20 through the container opening 18.

In another preferred embodiment of the present invention, the center portion of base 12 is elevated above the outer area of the base 12, as best shown in FIG. 3. Therefore, when a bathing solution is added to the container 10 to moisten and cleanse the coiled guide wire 20 stored within, the bathing solution will pool toward the outer edges of the container 10, where the coiled guide wire 20 is resting. This feature helps to conserve the bathing solution, because less is required to moisten and cleanse the coiled guide wire 20.

As shown in FIG. 6, the container 10 may also have vibrating means 26 attached to it, thereby transforming the container 10 into a type of ultrasonic cleaning container. That is, the vibrator 26 would vibrate the solution within the container 10, thus assuring that every portion of the coiled guide wire 20 is moistened and cleansed in between uses during the angiographic procedure. The container 10 of the present invention can be made from injection molded plastic, metal, or any other material as is known in the art.

In a preferred embodiment, the container 10 further has attachment means (not shown) such as double sided tape, clips, or other means of attachment, as is known in the art, so that the container 10 can be easily attached and secured to an area around a patient. This would insure that the coiled guide wire 20 within the container 10 remains nearby in between uses during the angiographic procedure, and would prevent the container 10 from tipping over or falling onto the floor, thereby minimizing contamination, As best shown in FIGS. 7 & 8, in another embodiment of the present invention, a plurality of containment chambers 36 can be provided, each nested inside the other. The inner nested chambers 38 may have either continuous or non-continuous sidewall portions 14. In order to insure that a coiled guide wire 20 is properly disposed within the proper chamber 36, an inner nested chamber 38 can have an outwardly extending lip portion 28, over which the coiled guide wire 20 can be hung, and then dropped into the next outer-most nested chamber 40. This embodiment allows for the simultaneous storing and cleansing of multiple guide wires 20. By nesting the chambers 36, the various guide wires 20 can be maintained separately.

As best shown in FIGS. 9 & 10, in another embodiment of the present invention, a plurality of guide rails 30 extend upwardly and inwardly from the base 12 of the container 10. The upper edges (not shown) of the guide rails 30 form an opening 18 into which the coiled guide wire 20 is placed. Once released, the potential energy in the coiled wire 20 will drive it into the base 12 of the container 10, as has already been described. The side walls 34 surround the guide rails 30 in order to contain a bathing solution disposed within. In this embodiment, the side walls 34 are not necessary to contain the coiled guide wire 20.

The container 10 of the present invention can be used to store, cleanse and moisten guide wires 20 between uses during angiography. When the guide wire 20 is removed from the patient, it is wiped to clean adherent blood, coiled, and dropped into the container 10 where it settles to the bottom 12 and is cleansed and moistened. When the guide wire 20 is next needed, it is easily and quickly retrieved, premoistened. The present invention may improve embolic complications during angiography such as stroke, by cleaning the guide wire 20 between uses. The container 10 of the present invention also reduces the time required to handle the guide wire 20, thereby minimizing angiography procedure time, important in reducing patient morbidity and mortality associated with the angiography procedure. This invention also contemplates use with catheters, as well as any elongated, flexible medical device requiring storage and/or cleansing.

Having described my invention, however, many modifications thereto will become apparent to those skilled in the art to which it pertains without deviation from the spirit of the invention as defined by the scope of the appended claims.

What is claimed is:

1. A guide wire container used in angiographic procedures, said container comprising:

a base having an interior surface, said interior surface having a central portion and an outer portion surrounding said central portion, at least one side wall extending both upwardly and inwardly from said base, each said side wall having an upper edge, said upper edge of each said side wall forming an opening, said opening dimensioned to receive and remove therethrough a guide wire provided in a coiled arrangement wherein a cross-sectional area of said opening is smaller than a cross-sectional area of said base.

2. The container of claim 1 further comprising a plurality of stand-off members extending upwardly from said interior surface of said base of said container.

3. The container of claim 2 wherein said stand-off members extend inwardly from an interior surface of said side wall of said container.

4. The container of claim 1 wherein said center portion of said base is elevated above said outer portion of said base surrounding said center portion.

5. The container of claim 1 further comprising at least one finger slot, each said finger slot comprising a protrusion extending downwardly from said opening to a point proximate said base.

6. The container of claim 1 further comprising a bathing solution disposed within said container.

7. The container of claim 6 further comprising means for vibrating said bathing solution within said container.

8. The container of claim 1 wherein said container further comprises injection molded plastic.

9. The container of claim 1 further comprising means for attaching said container to an area around a patient.

10. The container of claim 1 further comprising a plurality of nested chambers, said nested chambers comprising an inner chamber and an outer chamber, said inner chamber having an upper edge.

11. The container of claim 10 wherein said inner chamber further comprises non-continuous sidewall portions having spaces therebetween.

12. The container of claim 10 wherein said upper edge of said inner chamber further comprises an outwardly extending lip.

13. A guide wire container used in angiographic procedures, said container comprising:

a base having an upper surface, said upper surface having a central portion and an outer portion surrounding said central portion, and a plurality of elongated guide rails, each having an upper end, said guide rails extending both upwardly and inwardly from said base, said upper ends of said guide rails forming an opening, said opening dimensioned to receive and remove therethrough a guide wire provided in a coiled arrangement, wherein a cross-sectional area of said opening is smaller than a cross-sectional area of said base.

14. The container of claim 13 further comprising at least one side wall continuously surrounding said guide rails and attached to said upper surface of said base.

15. The container of claim 13 wherein said center portion of said base is elevated above said outer portion of said base surrounding said center portion.

16. The container of claim 13 further comprising a bathing solution contained within said container.

17. The container of claim 16 further comprising means for vibrating said bathing solution within said container.

18. The container of claim 13 wherein said container further comprises injection molded plastic.

19. The container of claim 13 further comprising means for attaching said container to an area around a patient.

20. In combination with an elongated, flexible medical device, a container for storing said device, said container comprising:

a base having an interior surface, said interior surface having a central portion and an outer portion surrounding said central portion, at least one side wall extending both upwardly and inwardly from said base, each said side wall having an upper edge, said upper edge of said side wall forming an opening, said opening dimensioned to receive and remove therethrough said medical device provided in a coiled arrangement, wherein a cross-sectional area of said opening is smaller than a cross-sectional area of said base.

21. The container of claim 20 further comprising a plurality of stand-off members extending upwardly from said interior surface of said base of said container.

22. The container of claim 21 wherein said stand-off members extend inwardly from an interior surface of said side wall of said container.

23. The container of claim 20 wherein said center portion of said base is elevated above said outer portion of said base surrounding said center portion.

24. The container of claim 20 further comprising at least one finger slot, each said finger slot comprising a protrusion extending downwardly from said opening to a point proximate said base.

25. The container of claim 20 further comprising a bathing solution contained within said container.

26. The container of claim 25 further comprising means for vibrating said bathing solution within said container.

27. The container of claim 20 wherein said container further comprises injection molded plastic.

28. The container of claim 20 further comprising means for attaching said container to an area around a patient.

29. A method of containing an elongated, flexible medical device in between medical procedures, said method comprising the steps of:

removing an elongated flexible medical device from a patient, coiling said medical device, disposing said coiled medical device in a container, said container comprising a base, and at least one side wall extending both upwardly and inwardly from said base, each said side wall having an upper edge, said upper edge of said side wall forming an opening, said opening dimensioned to receive and remove therethrough said medical device provided in a coiled arrangement, wherein a cross-sectional area of said opening is smaller than a cross-sectional area of said base.

30. The method of claim 29, further comprising the step of bathing said medical device in a bathing solution disposed within said container.

31. The method of claim 30, further comprising the step of vibrating said medical device within said bathing solution.

* * * * *